(12) United States Patent
Sun et al.

(10) Patent No.: US 8,884,082 B2
(45) Date of Patent: *Nov. 11, 2014

(54) SELECTIVE CATALYTICAL DEHYDROCHLORINATION OF HYDROCHLOROFLUOROCARBONS

(75) Inventors: Xuehui Sun, Swedesboro, NJ (US); Mario Joseph Nappa, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/397,967

(22) Filed: Feb. 16, 2012

(65) Prior Publication Data

US 2012/0215036 A1 Aug. 23, 2012
US 2014/0012048 A9 Jan. 9, 2014

Related U.S. Application Data

(60) Provisional application No. 61/444,868, filed on Feb. 21, 2011.

(51) Int. Cl.
C07C 17/25 (2006.01)
C07C 21/18 (2006.01)
C07C 19/10 (2006.01)
B01J 21/18 (2006.01)
B01J 37/08 (2006.01)
B01J 37/06 (2006.01)

(52) U.S. Cl.
CPC ............... *C07C 17/25* (2013.01); *B01J 21/18* (2013.01); *B01J 37/084* (2013.01); *B01J 37/06* (2013.01)
USPC ............ 570/156; 570/155; 570/226; 570/227

(58) Field of Classification Search
USPC .................. 570/155, 156, 226, 227
See application file for complete search history.

(56) References Cited

U.S. PATENT DOCUMENTS

| 2,898,383 | A | 8/1959 | Eisenlohr |
| 3,631,207 | A | 12/1971 | Kircher et al. |
| 4,978,649 | A | 12/1990 | Surovikin et al. |
| 5,136,113 | A | 8/1992 | Rao |
| 7,829,748 | B1 | 11/2010 | Tung et al. |
| 7,884,254 | B2 | 2/2011 | Wang et al. |
| 7,897,823 | B2 | 3/2011 | Miller et al. |
| 7,943,015 | B2 | 5/2011 | Rao et al. |
| 7,985,884 | B2 | 7/2011 | Nappa et al. |
| 8,178,466 | B2 | 5/2012 | Wang et al. |
| 2006/0106263 | A1 | 5/2006 | Miller et al. |
| 2007/0129579 | A1 | 6/2007 | Wang et al. |
| 2007/0197842 | A1 | 8/2007 | Mukhopadhyay et al. |
| 2009/0043137 | A1* | 2/2009 | Wang et al. ............ 570/136 |
| 2009/0149680 | A1 | 6/2009 | Wang et al. |
| 2009/0299107 | A1 | 12/2009 | Wang et al. |
| 2010/0312025 | A1* | 12/2010 | Nappa et al. ............ 570/157 |
| 2012/0215035 | A1 | 8/2012 | Nappa |
| 2012/0215037 | A1 | 8/2012 | Sun et al. |

FOREIGN PATENT DOCUMENTS

| CA | 2 608 327 | A1 | 4/2008 |
| CN | 101260021 | A | 9/2008 |
| CN | 101772480 | A | 7/2010 |
| FR | 2933691 | A1 * | 1/2010 |
| WO | WO 2008040969 | A2 * | 4/2008 |
| WO | 2008054781 | A1 | 5/2008 |
| WO | WO 2008075017 | A2 * | 6/2008 |
| WO | 2009015304 | A1 | 1/2009 |
| WO | WO 2009/009421 | A1 | 1/2009 |
| WO | 2009021154 | A2 | 2/2009 |
| WO | WO 2009/018561 | A2 | 2/2009 |
| WO | 2009125199 | A2 | 10/2009 |

OTHER PUBLICATIONS

Dubois, J-L et. al. English translation of patent No. FR 2933691A1.*
U.S. Office Action dated Feb. 21, 2013 for U.S. Appl. No. 13/370,337.
Chinese Office Action and Search Report issued in Application No. 201280009829.7 dated Jul. 29, 2014 (English translation only).

* cited by examiner

*Primary Examiner* — Jafar Parsa
*Assistant Examiner* — Medhanit Bahta
(74) *Attorney, Agent, or Firm* — Scully, Scott, Murphy & Presser, P.C.

(57) ABSTRACT

A dehydrochlorination process is disclosed. The process involves contacting $R_fCHClCH_2Cl$ with a carbon catalyst in a reaction zone to produce a product mixture comprising $R_fCCl=CH_2$, wherein $R_f$ is a perfluorinated alkyl group.

6 Claims, No Drawings

SELECTIVE CATALYTICAL DEHYDROCHLORINATION OF HYDROCHLOROFLUOROCARBONS

BACKGROUND

1. Field of the Disclosure

This disclosure relates in general to the selective catalytic dehydrochlorination of hydrochlorofluorocarbons (HCFCs) to make hydrochlorofluoroolefins (HCFOs). More specifically, the catalysts are carbons.

2. Description of Related Art

Hydrochlorofluoroolefins (HCFOs), having low ozone depletion potential and low global warming potentials, are regarded as candidates for replacing saturated CFCs (chlorofluorocarbons) and HCFCs (hydrochlorofluorocarbons). HCFOs can be employed in a wide range of applications, including their use as refrigerants, solvents, foam expansion agents, cleaning agents, aerosol propellants, dielectrics, fire extinguishants and power cycle working fluids. For example, HCFO-1233xf ($CF_3CCl=CH_2$) can be used as a foam expansion agent, fire extinguishant, refrigerant, et al. HCFO-1233xf is also an intermediate in the production of 2,3,3,3-tetrafluoropropene (HFO-1234yf) which is a refrigerant with zero ozone depletion potential and low global warming potential.

BRIEF SUMMARY OF THE DISCLOSURE

The present disclosure provides a dehydrochlorination process. The process comprises contacting $R_fCHClCH_2Cl$ with a carbon catalyst in a reaction zone to produce a product mixture comprising $R_fCCl=CH_2$, wherein $R_f$ is a perfluorinated alkyl group.

DETAILED DESCRIPTION

The foregoing general description and the following detailed description are exemplary and explanatory only and are not restrictive of the invention, as defined in the appended claims. Other features and benefits of any one or more of the embodiments will be apparent from the following detailed description, and from the claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

The term "dehydrochlorination", as used herein, means a process during which hydrogen and chlorine on adjacent carbons in a molecule are removed.

The term "hydrochlorofluoroolefin", as used herein, means a molecule containing hydrogen, carbon, fluorine, chlorine, and at least one carbon-carbon double bond. Exemplary hydrochlorofluoroolefins in this disclosure include HCFO-1233xf.

The term "alkyl", as used herein, either alone or in compound words such as "perfluorinated alkyl group", includes cyclic or acyclic and straight-chain or branched alkyl groups, such as, methyl, ethyl, n-propyl, i-propyl, or the different isomers thereof.

The term "perfluorinated alkyl group", as used herein, means an alkyl group wherein all hydrogens on carbon atoms have been substituted by fluorines. Examples of a perfluorinated alkyl group include $—CF_3$ and $—CF_2CF_3$.

The term "product selectivity to $R_fCCl=CH_2$", as used herein, means the molar percentage of $R_fCCl=CH_2$ obtained in the process compared to the total molar amounts of all products obtained.

The term "dehydrochlorination selectivity to $R_fCCl=CH_2$", as used herein, means the molar percentage of $R_fCCl=CH_2$ based on the total molar amount of $R_fCCl=CH_2$ and $R_fCH=CHCl$ obtained in the dehydrochlorination reaction of $R_fCHClCH_2Cl$.

The term "an elevated temperature", as used herein, means a temperature higher than the room temperature.

Disclosed is a dehydrochlorination process comprising contacting $R_fCHClCH_2Cl$ with a carbon catalyst in a reaction zone to produce a product mixture comprising $R_fCCl=CH_2$, wherein $R_f$ is a perfluorinated alkyl group.

In some embodiments of this invention, $R_f$ is $—CF_3$ or $—CF_2CF_3$. In some embodiments of this invention, $R_fCHClCH_2Cl$ is $CF_3CHClCH_2Cl$ (HCFC-243 db), and $R_fCCl=CH_2$ is $CF_3CCl=CH_2$ (HCFO-1233xf).

Some hydrochlorofluoroolefins of this disclosure, e.g., $CF_3CH=CHCl$ (HCFO-1233zd), exist as different configurational isomers or stereoisomers. When the specific isomer is not designated, the present disclosure is intended to include all single configurational isomers, single stereoisomers, or any combination thereof. For instance, HCFO-1233zd is meant to represent the E-isomer, Z-isomer, or any combination or mixture of both isomers in any ratio.

The starting materials for the dehydrochlorination processes in this disclosure, i.e., $R_fCHClCH_2Cl$, can be synthesized by methods known in the art. For example, HCFC-243 db may be prepared by chlorinating $CF_3CH=CH_2$ or by the addition reaction of $CF_2=CHCl$ with $CFClH_2$.

The dehydrochlorination process can be carried out in liquid phase or vapor phase using well-known chemical engineering practice, which includes continuous, semi-continuous or batch operations. The temperature in the reaction zone is typically from about 300° C. to about 500° C. In some embodiments of this invention, the temperature in the reaction zone is from about 325° C. to about 450° C. The dehydrochlorination process can be conducted at superatmospheric, atmospheric, or subatmospheric pressures. The contact time of the starting material $R_fCHClCH_2Cl$ with the catalyst can be largely varied. Typically, the contact time is from about 10 seconds to about 150 seconds. In some embodiments of this invention, the contact time is from about 20 seconds to about 80 seconds.

The contacting step of this invention may be carried out by methods known in the art. In some embodiments of this invention, starting material $R_fCHClCH_2Cl$, optionally with an inert gas, is fed to a reactor containing the catalyst. In some embodiments of this invention, starting material $R_fCHClCH_2Cl$, optionally with an inert gas, is passed through the catalyst bed in a reactor. In some embodiments of this invention, starting material $R_fCHClCH_2Cl$, optionally with an inert gas, may be mixed with the catalyst in a reactor with stir or agitation.

The dehydrochlorination process may be conducted in the presence of an inert gas such as He, Ar, or $N_2$. In some embodiments of this invention, the inert gas is co-fed into the reactor with the starting material.

It was found through experiments that carbons are suitable for selective dehydrochlorination process of this disclosure. Carbon used in the embodiments of this invention may come from any of the following sources: wood, peat, coal, coconut shells, bones, lignite, petroleum-based residues and sugar. Commercially available carbons which may be used include those sold under the following trademarks: Barneby & Sutcliffe™, Darco™, Nucharm, Columbia JXN™, Columbia LCK™, Calgon™ PCB, Calgon™ BPL, Westvaco™, Norit™, Takeda™ and Barnaby Cheny NB™.

The carbon also includes three dimensional matrix porous carbonaceous materials. Examples are those described in U.S. Pat. No. 4,978,649. In one embodiment of the invention, carbon includes three dimensional matrix carbonaceous materials which are obtained by introducing gaseous or vaporous carbon-containing compounds (e.g., hydrocarbons) into a mass of granules of a carbonaceous material (e.g., carbon black); decomposing the carbon-containing compounds to deposit carbon on the surface of the granules; and treating the resulting material with an activator gas comprising steam to provide a porous carbonaceous material. A carbon-carbon composite material is thus formed.

Embodiments of carbon in this invention include both non-acid washed and acid-washed carbons. In some embodiments of this invention, suitable carbon catalysts may be prepared by treating the carbon with acids such as $HNO_3$, HCl, HF, $H_2SO_4$, $HClO_4$, $CH_3COOH$, and combinations thereof. Acid treatment is typically sufficient to provide carbon that contains less than 1000 ppm of ash. Some suitable acid treatments of carbon are described in U.S. Pat. No. 5,136,113. In some embodiments of this invention, an activated carbon is dried at an elevated temperature and then is soaked for 8 to 24 hours with occasional stirring in 1 to 12 weight percent of $HNO_3$. The soaking process can be conducted at temperatures ranging from room temperature to 80° C. The activated carbon is then filtered and washed with deionized water until the washings have a pH greater than 4.0 or until the pH of the washings does not change. Finally, the activated carbon is dried at an elevated temperature.

In some embodiments of this invention, carbon is an activated carbon. In some embodiments of this invention, carbon is a non-acid washed activated carbon. In some embodiments of this invention, carbon is an acid washed activated carbon. The carbon can be in the form of powder, granules, or pellets, et al.

The effluent from the reaction zone typically includes residual starting materials $R_fCHClCH_2Cl$, desired hydrochlorofluoroolefin product $R_fCCl=CH_2$, dehydrochlorination byproduct $R_fCH=CHCl$ and some other byproducts. The desired product $R_fCCl=CH_2$ may be recovered from the product mixture by conventional methods. In some embodiments of this invention, product $R_fCCl=CH_2$ may be purified or recovered by distillation.

It was found through experiments that the catalytic dehydrochlorination processes of this disclosure produced desired products with high selectivity. In some embodiments of this invention, the product selectivity to $R_fCCl=CH_2$ is at least 90 mole %.

It was also found through experiments that the dehydrochlorination reaction of this disclosure is highly selective. The dehydrochlorination reaction of $R_fCHClCH_2Cl$ may generate both isomers $R_fCCl=CH_2$ and $R_fCH=CHCl$. It was found that the dehydrochlorination processes of this disclosure generate substantially more $R_fCCl=CH_2$ than $R_fCH=CHCl$. In some embodiments of this invention, the dehydrochlorination selectivity to $R_fCCl=CH_2$ is at least 95 mole %.

The reactors, distillation columns, and their associated feed lines, effluent lines, and associated units used in applying the processes of embodiments of this invention may be constructed of materials resistant to corrosion. Typical materials of construction include Teflon™ and glass. Typical materials of construction also include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

Many aspects and embodiments have been described above and are merely exemplary and not limiting. After reading this specification, skilled artisans appreciate that other aspects and embodiments are possible without departing from the scope of the invention.

EXAMPLES

The concepts described herein will be further described in the following examples, which do not limit the scope of the invention described in the claims.

Example 1

Example 1 demonstrates that contacting HCFC-243 db with carbon generates HCFO-1233xf.

5 cc (cubic centimeter) (2.78 gm) of Calgon™ non-acid washed PCB carbon (an activated carbon with surface area ranging from about 900 $m^2/g$ to about 1200 $m^2/g$) (12-30 mesh) were filled into an Inconel™ reactor tube (0.43 inch ID) to form a catalyst bed.

The reactor tube temperature was then raised to about 400° C. HCFC-243 db was fed into a vaporizer at 1.62 ml/hour and was vaporized at 94° C. Nitrogen was flowed through the vaporizer at 3.6 sccm and carried vaporized HCFC-243 db to the reactor tube. Product samples were taken at one hour intervals and analyzed by GC-MS and tabulated as mole percentage. The remaining percentages were unknown byproducts.

TABLE 1

| Temp °C. | 243db ml/hr | N₂ sccm | CT sec | Conv Mole % 243db | Prod Sel Mole % 1233xf | Prod Sel Mole % 1233zd | Prod Sel Mole % 253fb | DHC Sel Mole % 1233xf |
|---|---|---|---|---|---|---|---|---|
| 401 | 1.62 | 3.6 | 32 | 100.0% | 91.1% | 4.9% | 0.6% | 95 |
| 401 | 1.62 | 3.6 | 32 | 100.0% | 91.0% | 4.8% | 0.6% | 95 |
| 400 | 1.62 | 3.6 | 32 | 100.0% | 90.5% | 4.8% | 0.6% | 95 |

Note:
Temp = Temperature;
ml = milliliter;
hr = hour;
CT = Contact Time;
Conv = Conversion;
Sel = Selectivity;
Prod = Product;
DHC = Dehydrochlorination;
243db = HCFC-243db;
1233xf = HCFO-1233xf;
1233zd = HCFO-1233zd;
253fb = HCFC-253fb = CH₂ClCH₂CF3.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination.

What is claimed is:

1. A dehydrochlorination process comprising contacting $R_fCHClCH_2Cl$ with a carbon catalyst in a reaction zone to produce a product mixture comprising $R_fCCl=CH_2$, wherein $R_f$ is a perfluorinated alkyl group, wherein the temperature in the reaction zone ranges from about 325° C. to about 500° C. and wherein the product selectivity to $R_fCCl=CH_2$ is at least 90 mole %.

2. The dehydrochlorination process of claim 1 wherein the carbon catalyst is an activated carbon.

3. The dehydrochlorination process of claim 2 wherein the carbon catalyst is an acid washed activated carbon.

4. The dehydrochlorination process of claim 2 wherein the carbon catalyst is a non-acid washed activated carbon.

5. The dehydrochlorination process of claim 1 wherein $R_f$ is $CF_3$.

6. The dehydrochlorination process of claim 1 wherein the dehydrochlorination selectivity to $R_fCCl=CH_2$ is at least 95 mole %.

* * * * *